United States Patent
Ketels et al.

(10) Patent No.: US 11,801,320 B2
(45) Date of Patent: Oct. 31, 2023

(54) VEHICLE SANITIZING SHIELD

(71) Applicant: Faurecia Interior Systems, Inc., Auburn Hills, MI (US)

(72) Inventors: Cedric Ketels, Mountain View, CA (US); Thomas Dessapt, Sunnyvale, CA (US)

(73) Assignee: Faurecia Interior Systems, Inc., Auburn Hills, MI (US)

(*) Notice: Subject to any disclaimer, the term of this patent is extended or adjusted under 35 U.S.C. 154(b) by 293 days.

(21) Appl. No.: 17/076,472

(22) Filed: Oct. 21, 2020

(65) Prior Publication Data

US 2022/0118143 A1    Apr. 21, 2022

(51) Int. Cl.
| | |
|---|---|
| A61L 2/26 | (2006.01) |
| B60J 9/04 | (2006.01) |
| B60R 15/00 | (2006.01) |
| B60H 3/00 | (2006.01) |
| A61L 2/10 | (2006.01) |
| A61L 9/20 | (2006.01) |
| A61L 2/00 | (2006.01) |

(52) U.S. Cl.
CPC ............... *A61L 2/26* (2013.01); *A61L 2/0088* (2013.01); *A61L 2/10* (2013.01); *A61L 9/20* (2013.01); *B60H 3/0071* (2013.01); *B60J 9/04* (2013.01); *B60R 15/00* (2013.01)

(58) Field of Classification Search
CPC ..... A61L 2/10; A61L 2/26; A61L 9/20; A61L 2/0088; B60J 9/04; B60R 15/00; B60H 3/0071

See application file for complete search history.

(56) References Cited

U.S. PATENT DOCUMENTS

| | | | |
|---|---|---|---|
| 7,202,484 B1* | 4/2007 | Tantillo | A61L 2/10 |
| | | | 34/209 |
| 8,602,257 B2 | 12/2013 | Godsell | |
| 2008/0283626 A1 | 11/2008 | Aldana et al. | |
| 2015/0367008 A1* | 12/2015 | Romo | A61L 9/20 |
| | | | 250/492.1 |
| 2019/0076558 A1 | 3/2019 | Zhang-Miske et al. | |
| 2021/0353969 A1* | 11/2021 | Leschinsky | A62B 9/00 |
| 2022/0062453 A1* | 3/2022 | Willis | A61L 2/0047 |

FOREIGN PATENT DOCUMENTS

| | | |
|---|---|---|
| EP | 2276582 B1 | 9/2019 |
| WO | WO2018225472 A1 | 12/2018 |
| WO | WO2020016587 A1 | 1/2020 |

* cited by examiner

*Primary Examiner* — Sean E Conley

(74) *Attorney, Agent, or Firm* — Reising Ethington P.C.

(57) ABSTRACT

A sanitizing shield for a vehicle includes a separation surface configured to at least partially shroud a shielded seat. The separation surface has an inner seat facing side and an outer shielding side. The sanitizing shield includes a sanitization station coupled to the separation surface. The sanitizing shield can have one or more of a hand sanitizer dispenser, an air purifier, and/or an ultraviolet-C (UVC) sanitizer. The sanitizing shield provides for improved physical separation within the passenger cabin while enhancing the sanitization potential available to rear passengers of the vehicle.

16 Claims, 3 Drawing Sheets

# VEHICLE SANITIZING SHIELD

TECHNICAL FIELD

The present disclosure is related generally to vehicle interiors and, more particularly, to privacy screens for vehicle interiors.

BACKGROUND

Privacy screens are oftentimes used in vehicles to physically isolate one or more vehicle passengers from the driver, and vice versa. While some privacy screens include features such as displays, as described in PCT Publication WO 2018/225472 to Shogo et al., the structure of the privacy screen itself in such implementations has the potential to be bulky and obtrusive. Providing a more streamlined and potentially modular solution is desirable, along with providing more sanitization-related enhancements to other passengers in the vehicle. Increasing in-vehicle sanitization capabilities can be particularly advantageous in ride sharing scenarios, for example.

SUMMARY

An illustrative sanitizing shield for a vehicle comprises a separation surface configured to at least partially shroud a shielded seat. The separation surface has an inner seat facing side and an outer shielding side. The sanitizing shield includes a sanitization station coupled to the separation surface.

In various embodiments, the sanitization station includes a hand sanitizer dispenser.

In various embodiments, the hand sanitizer dispenser is located in a recessed wall of the sanitization station.

In various embodiments, the sanitization station includes an air purifier.

In various embodiments, the air purifier includes one or more perimeter exhaust vents.

In various embodiments, the separation surface is configured to create an air curtain that at least partially surrounds the shielded seat.

In various embodiments, a concave contour in the separation surface is configured to create the air curtain.

In various embodiments, at least one perimeter exhaust vent is located on an outer sanitizing side of the sanitization station and at least one perimeter exhaust vent is located on an inner seat facing side of the sanitization station.

In various embodiments, the sanitization station includes an ultraviolet-C (UVC) sanitizer.

In various embodiments, the separation surface includes a plurality of removable panels attached to the sanitization station.

In various embodiments, the plurality of removable panels are situated around a centrally located sanitization station.

In various embodiments, each removable panel of the plurality of removable panels is made from a nonporous material.

In various embodiments, the sanitization station includes a carrier configured to accept a plurality of sanitization units.

In various embodiments, the plurality of sanitization units includes a hand sanitizer dispenser and an air purifier.

In various embodiments, the sanitization station has an inner seat facing side, and wherein a clamp plate is attached to the inner seat facing side of the sanitization station via a structural link that is configured to facilitate movement of the separation surface with respect to the shielded seat.

It is contemplated that any number of the individual features of the above-described embodiments and of any other embodiments depicted in the drawings or description below can be combined in any combination to define an invention, except where features are incompatible.

BRIEF DESCRIPTION OF THE DRAWINGS

Illustrative embodiments will hereinafter be described in conjunction with the following figures, wherein like numerals denote like elements, and wherein.

DESCRIPTION OF ILLUSTRATIVE EMBODIMENTS

Described herein is a sanitizing shield that is advantageously used in ride sharing or ride hailing vehicles, for example, to provide physical separation and privacy while increasing disinfection capabilities. The sanitizing shield provides for an installable compartmentalization solution, while improving disinfection capacity. Vehicle passenger cabin cleanliness and enhancing structural separation within the cabin can enhance vehicle users' experiences. The sanitizing shield includes a separation surface that shrouds a shielded seat, typically the driver's seat, and a sanitization station coupled to the separation surface. The separation surface provides a physical barrier and enhances cabin compartmentalization, while the sanitization station allows for disinfection of the cabin, the cabin air, and/or a passenger's hands.

With respect to the ride sharing scenario outlined above, throughout a rider's journey, there are numerous instances in which contact with the vehicle occurs. Upon ingress, contact is typically made with the exterior door handle, interior grab handles, the seat back or shoulder, and floor mats. Upon entry, contact is typically made with the interior door handle and various seat surfaces such as the knob, buckle, and belt of the seat belt. En route, contact is oftentimes made with a human machine interface (HMI), a display, and other rider-controllable features such as windows, storage compartments, etc. Arm rests and the top roll of the door panel may also be contacted. Upon egress, contact is typically made with the interior door handle, the interior grab handle, a seat back or shoulder, and the exterior door handle. Given this level of contact within the vehicle, it is advantageous to provide various ways in which sanitization and disinfection can occur in order to promote vehicle cleanliness and vehicle user confidence. Combining physical separation with multiple sanitization options in a modular in-vehicle unit can help accomplish these goals.

Figure 1:
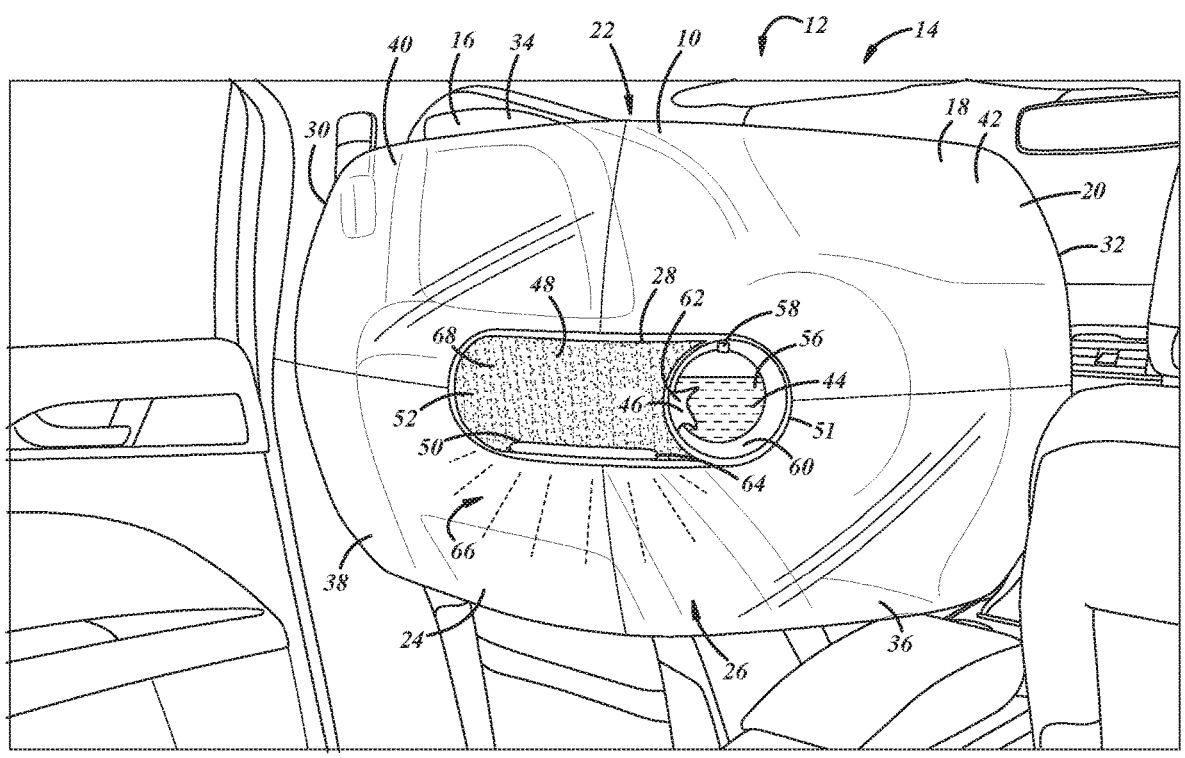
FIG. 1 illustrates a portion of a vehicle interior and a sanitizing shield according to one embodiment.

FIG. 1 illustrates a sanitizing shield 10 within an interior passenger cabin 12 of a vehicle 14. The sanitizing shield 10 shields the driver's seat 16 of the vehicle 14 (i.e., the driver's seat 16 is the shielded seat with respect to the sanitizing shield 10). While the present description is primarily focused on the sanitizing shield 10 being installed on the driver's seat 16, it may be possible to use the sanitizing shield to shroud other seats within the vehicle 14. However, installation on the driver's seat 16 can be particularly advantageous in a ride sharing scenario, as it can provide a physical barrier between the driver and any ride sharing passengers.

The sanitizing shield 10 includes a main blocking body 18 and separation surface 20 configured to at least partially shroud the shielded seat 16. The separation surface 20 has an inner seat facing side 22, an outer shielding side 24, and a concave contour 26. The concave contour 26, along the inner seat facing surface 22 of the sanitizing shield 10, forms a convex contour along the outer shielding surface 24. This structure of the concave contour 26 provides a more streamlined appearance and is less obtrusive, as its conformational shape takes up less space in the vehicle interior 12 than a typical planar or flat privacy screen. The sanitizing shield 10 also includes a sanitization station 28 coupled to the blocking body 18 and separation surface 20. The sanitization station 28, in at least the illustrated embodiment, has multiple sanitization modalities to facilitate within vehicle disinfection. Moreover, as opposed to more typical privacy screens in taxi cabs and limousines, the sanitizing shield 10 does not fully segregate the driver into another area within the passenger cabin 12. This can allow the driver in a ride-hailing or ride-sharing scenario to more easily switch between commercial and non-commercial usage of the vehicle 14.

The separation surface 20 includes a first saddle edge 30 and a second saddle edge 32 with the concave contour 26 extending therebetween. This structure can improve the shielding capacity of the shield 10 while minimizing obtrusiveness within the vehicle cabin 12 and maximizing interior space. In the embodiment for the driver's seat 16, the first saddle edge 30 of the sanitizing shield 10 is at least partially aligned with an outer edge of the headrest 34 (the outer edge facing towards the nearest door, which provides greater shielding capacity). The concave contour 26 of the shield 10 is aligned with the sanitization station 28, which is centrally located with respect to the separation surface 20. This arrangement helps centrally locate the sanitization station 28 in a more optimal location to promote accessibility to a rider in the rear of the cabin 12, and also can provide for more streamlined compartmentalization of the cabin by conformally orienting the concave contour 26 with the structure of the seat 16.

The separation surface 20 comprises a plurality of removable panels 36, 38, 40, 42. Having the shield 10 be modularly removable and fully detachable allows for after-market potential, and may be better in ride-sharing or ride-hailing scenarios. However, it is possible to have a more unitary separation surface 20 that is not subdivided into a plurality of panels. Thus, it is possible for the separation surface 20 to be fixed, removable, and/or extendable. In one example, the separation surface is a semi-rigid panel that can be retracted when needed, through mechanical joints such as pivots or sliders or via origami-based techniques (e.g., the separation surface is foldable). As shown more particularly in FIGS. 2 and 3, in the illustrated embodiments, the panels 36, 38, 40, 42 are coupled to and selectively removable with respect to the centrally located sanitization station 28. Thus, a driver or other vehicle user can remove one or more panels, such as the upper panels 40, 42 in certain instances, one such possible instance being when the vehicle 14 is not being used for ride sharing. With embodiments having multiple panels 36, 38, 40, 42, each panel should be proportionally sized to facilitate adequate shrouding of the seat 16 and physical isolation between vehicle occupants. In the illustrated embodiment, the panels are generally the same size, with the panel 36 sized to block the torso of the driver, the panel 38 sized to block the back of the seat 16, the panel 40 sized to block the headrest 34, and the panel 42 sized to block the face of the driver. Depending on the number of panels, the separation surface 20 as a whole can be sized to block these various regions in the cabin 12 to enhance compartmentalization within the vehicle 14.

The separation surface 20, and accordingly the removable panels 36, 38, 40, 42, can be made of any operable material, but advantageously, the separation surface 20 is rigid and nonporous, allowing for easy disinfection and providing a more anti-bacterial surface. Example nonporous materials for the separation surface 20 includes varnished wood, acrylic or plexiglass, PVC, or another rigid plastic. The separation surface 20 may be made from a single sheet or layer of material, or in some embodiments, may have a multi-layer structure (e.g., a sound dampening foam material between two outer skin layers). In some implementations, parts or subcomponents of the separation surface 20 may be made of one material, while the remainder of the separation surface is made of a different material. In yet other implementations, such as that illustrated in FIG. 1, all or a portion of the separation surface 20 is a matte translucid surface. This can help limit dirt and finger marks, while maintaining partial visibility. In this embodiment, the separation surface 20 is "light-transmissive," meaning that at least some light can pass through the separation surface. Light transmissive may include any non-opaque configuration, such as one that is transparent, translucent, semi-transparent, semi-translucent, etc. A coating or the like that helps to reduce the transmission or bacteria and/or viruses may also be used. Hygienic configurations (e.g., smoother surfaces, less grooves, etc.) can be beneficial as well. Other example materials and configurations for the separation surface 20 are certainly possible.

The separation surface 20 can include other more aesthetic and/or functional features as well. For example, a diffuser may be included to achieve a desired backlit appearance. A projector can be included to project an image or video onto the surface 20, or another display can be implemented with the shield 10. The display may show a message relating to the level of vehicle sanitization (e.g., a visual confirmation that disinfection of the cabin 12 has occurred). The outer shielding side 24 can include advertising or branding, which can provide additional revenue streams when the vehicle 14 is used in ride sharing scenarios. Light strips creating light effects can enhance perceived quality and a sensation of cleanliness through specific color displays. A power cord can provide energy to the shield 10 and connect the shield to the power supply of the vehicle (e.g., via the cigarette lighter). If the shield 10 is connected to the vehicle power supply, it may include other energy-based features such as a mobile device charger.

The sanitizing shield 10 includes a sanitization station 28 configured to provide active disinfection capabilities within the vehicle 14. In some embodiments, the sanitization station 28 is a modular feature including a carrier that can be adapted and changed depending on the level of desired in-vehicle sanitization. In other embodiments, the sanitization station does not have a separate carrier, and instead, the various features can be dispersed from each other along the separation surface. Features for the sanitization station 28 include, but are not limited to, a hand sanitizer dispenser 44, a sanitizing wipes dispenser 46, an air purifier 48, and an ultraviolet-C (UVC) sanitizer 50. Other potential features include a separate mask sanitizer and/or a mask dispenser, to cite a few examples. Hydrogen peroxide fogging and/or heat treatment capabilities can be implemented to help bolster disinfection potential. In some embodiments, features for providing proof of sanitization are provided. Those can include, but are not limited to visual types of confirmation (e.g., a multi-modal HMI displays a sanitization complete message after the UVC sanitizer is run) and olfactory types of confirmation (e.g., fragrance-based enhancement to the air purifier 48).

Figure 4:
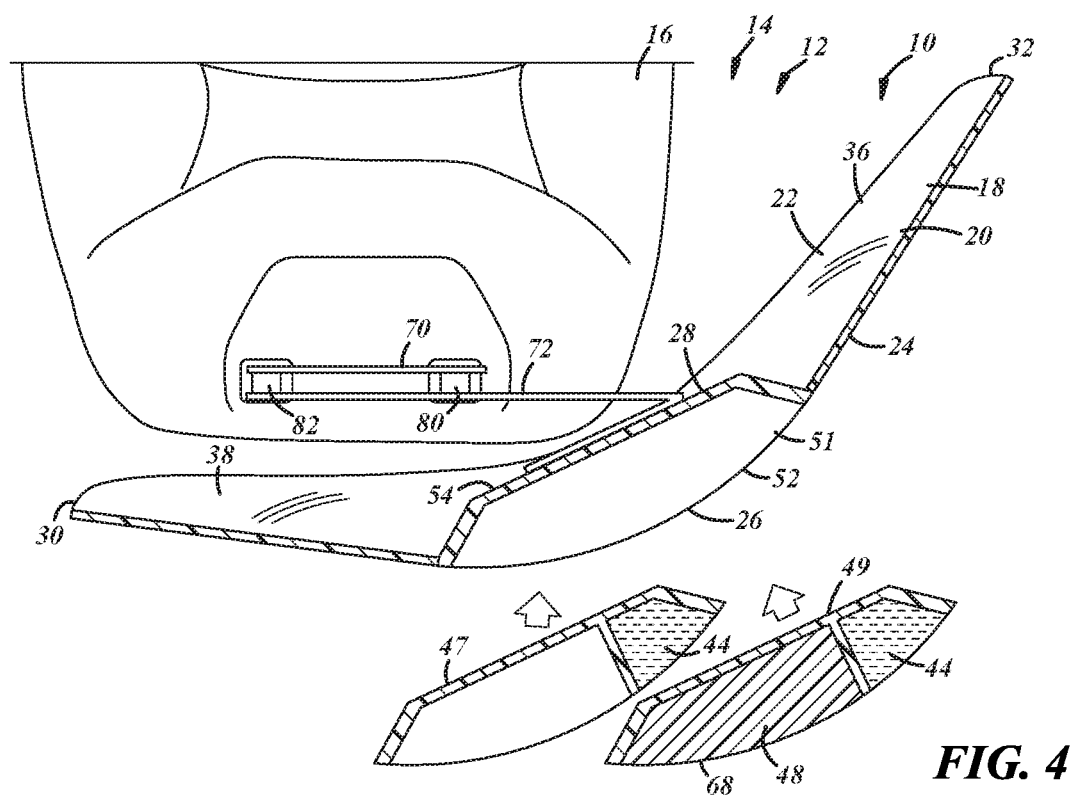
FIG. 4 is a partial, cross-section view of a sanitizing shield having removable sanitization units.

Advantageously, the sanitization station 28 provides the ability for disinfecting or sanitizing a vehicle occupant's hands, one or more surfaces within the cabin 12, and the cabin air from particles, germs, and/or viruses. However, it is possible in some implementations to have more limited sanitization functionality, which can impact the overall cost of the shield 10. For example, in some implementations, the sanitization station 28 may only include a hand sanitizer dispenser. One or more of the features of the sanitization station 28 described herein can be included as removable sanitization units 47, 49 that are installable in a carrier 51, as shown in the partial, cross-section view of a sanitizing shield 10 in FIG. 4. This allows for a base carrier 51 to be customized depending on the desired functionality and cost structure for the overall shield 10. For example, the carrier 51 may be fitted with a removable sanitization unit 47 that has only the hand sanitizer dispenser 44 as described above, and an air purifier sanitization unit can be purchased and installed in the carrier 51 separately if desired. A different removable sanitization unit 49 may be used in some implementations, which includes both the hand sanitizer dispenser 44 and the air purifier 48. The removable sanitization units 47, 49 may click into (e.g., via a locking detent or the like) the carrier 51 or otherwise be installable with respect to the sanitization station 28. This interchangeability is beneficial with particular features, such as the hand sanitizer dispenser 44, as a user can easily install a new hand sanitizer cartridge or dispenser, for example. Other combinations and features for the removable sanitization units 47, 49 are certainly possible, such as a sanitizing wipes dispenser with a UVC sanitizer, or just a UVC sanitizer, to cite a few examples.

Returning to the embodiment illustrated in FIG. 1, the sanitization station 28 includes an outer sanitizing side 52 and an inner seat facing side 54. The sanitization features such as the hand sanitizer dispenser 44, the sanitizing wipes dispenser 46, the air purifier 48, and the ultraviolet-C (UVC) sanitizer 50 are generally available on the outer sanitizing side 52 of the sanitization station 28. When the shield 10 is installed on the driver's seat 16, the sanitization station 28 can be positioned such that the outer sanitizing side 52, and accordingly, the sanitization features, are easily accessible to one or more passengers in the rear seats of the vehicle 14. As detailed more fully below, the inner seat facing side 54 of the sanitization station 28 can be used as the structural carrier element for attaching the shield 10 to the seat 16 or another portion of the vehicle 14.

The hand sanitizer dispenser 44 includes a reservoir 56 for storing hand sanitizer, such as an alcohol-based sanitizer, with a pump and/or nozzle 58 for dispensing the sanitizer. In the illustrated embodiment, the hand sanitizer dispenser 44 is a hydroalcoholic gel dispenser situated for easy use by a passenger in one of the rear seats of the vehicle 14. The reservoir 56 for storing the sanitizer may be light-transmissive in order to visibly display the remaining level of sanitizer. The hand sanitizer dispenser 44 may be a passive, manually operated dispenser. In other embodiments, the hand sanitizer dispenser 44 has power-based features such as automatic hand detection which triggers automatic dispensing. Accordingly, a sensor can be included to detect hand presence and trigger sanitizer distribution. This particular embodiment includes a recessed wall 60 which serves as a sanitizer receiver for misuses or over-dispensed sanitizer. Upon ingress, a ride sharing passenger, for example, can easily sanitize his or her hands before contacting various portions of the rear seating area of the cabin 12.

The sanitizing wipes dispenser 46 may be included to provide disinfecting wipes 62 that can be used to wipe down various areas of the vehicle cabin 12. In other embodiments, the dispenser 46 may dispense disposable masks or some other feature that helps promote in-vehicle sanitization. The example embodiment of FIG. 1 shows the sanitizing wipes dispenser 46 integrated with the recessed wall 60 of the hand sanitizer dispenser 44. However, it is possible to include the dispenser 46 at a different location within the sanitization station 28. Further, in some embodiments, there may not be a separate hand sanitizer dispenser 44, and instead, skin and object-safe disinfection wipes can be dispensed via a single sanitizing wipes dispenser 46.

The air purifier 48 can provide pollution filtration to clean the air of the cabin 12. In one example, the air purifier 48 includes a PM2.5 filter to help facilitate air disinfection. More particularly, the filter of the air purifier 48 can be an advance, multi-layer filter that filters out bacteria, as well as most pollen, dust, fungal spores, and VOCs. A pollution sensor can be included to help ascertain air quality. A fragrance dispenser can also be included to spread a pleasing and/or branded scent in the vehicle cabin 12. An internal fan and/or air ducts within the air purifier 48 help promote air flow through the sanitization station 28 and into the vehicle cabin 12 via exhaust vents 53, 55 and/or an air outlet 68. The air outlet 68 can be located on either or both of the outer sanitizing side 52 and the inner seat facing side 54 of the sanitization station 28. Locating an air outlet 68 on the outer sanitizing side 52 directs purified air in a more targeted fashion toward the rear seats and rear passengers in the vehicle cabin 12. Locating an air outlet on the inner seat facing side 54 directs purified air in a more targeted fashion toward the driver of the vehicle in the driver's seat 16.

Figure 2:
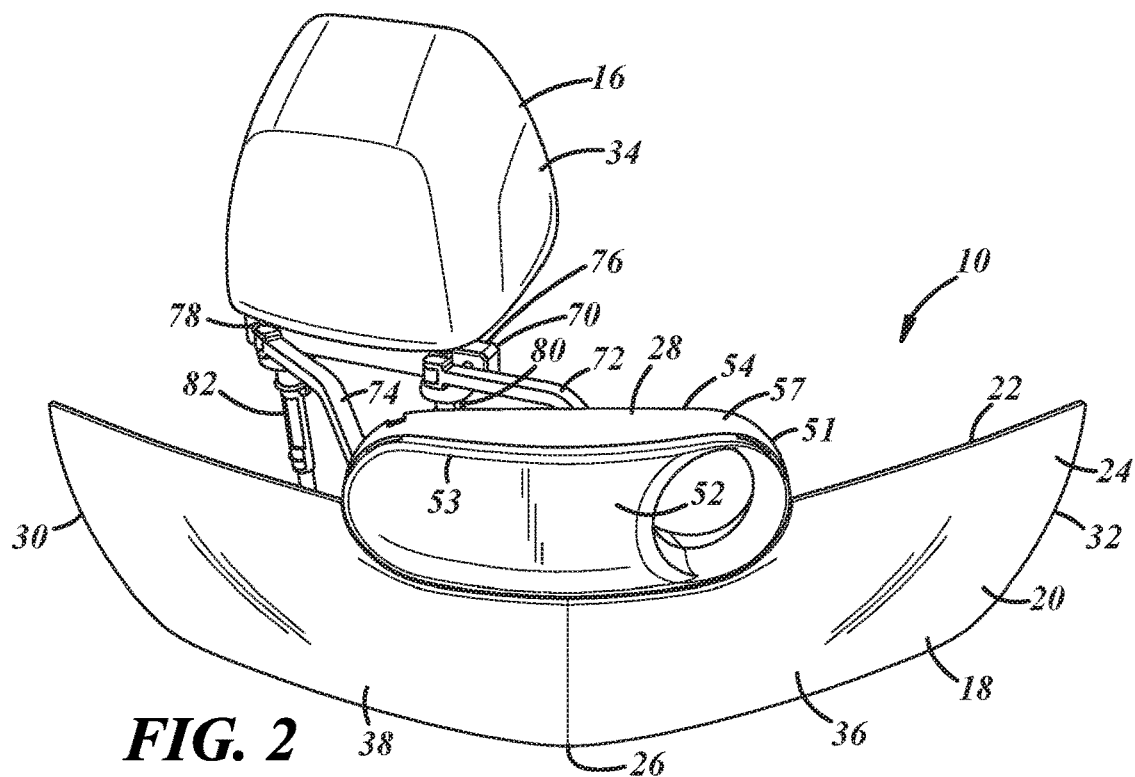
FIG. 2 illustrates a sanitizing shield and a head rest of a vehicle seat according to another embodiment.
Figure 3:
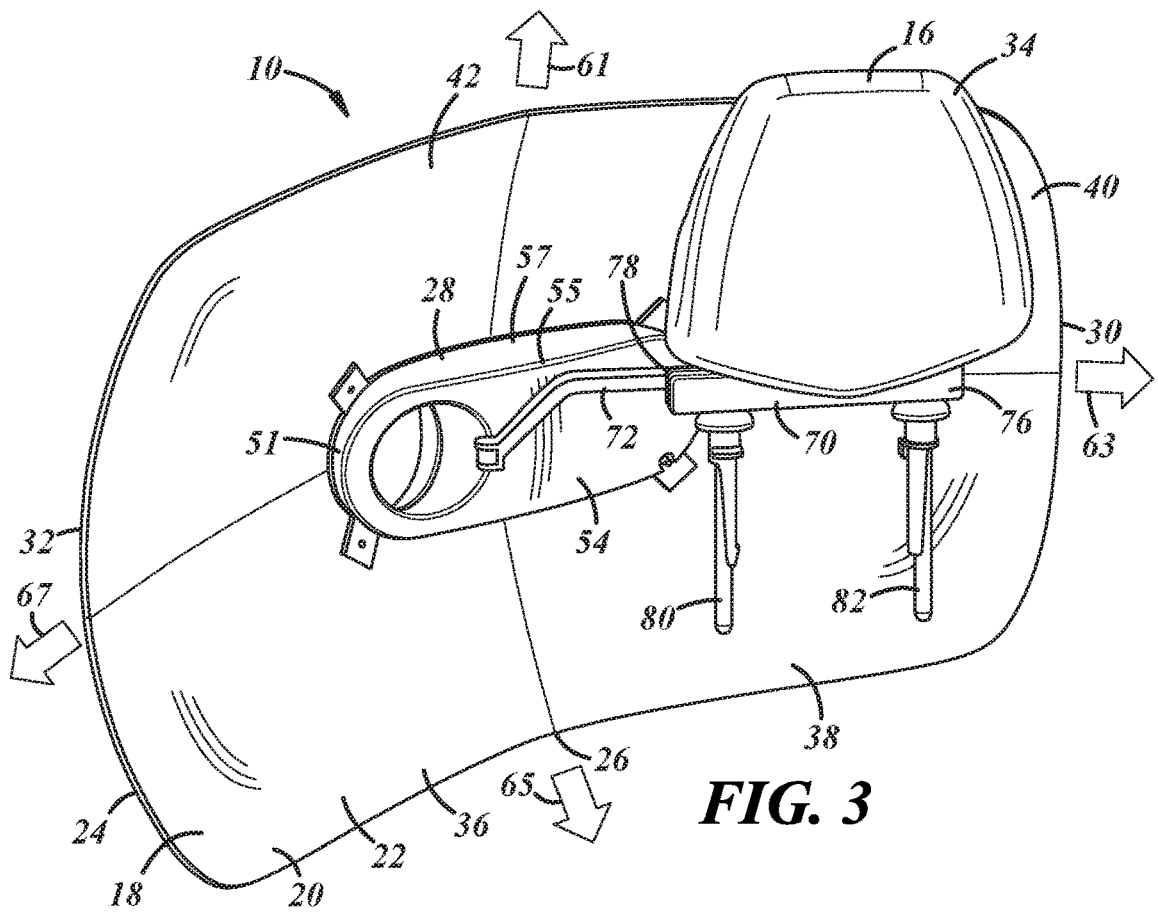
FIG. 3 illustrates the inner seat facing side of the sanitizing shield of FIG. 2.

With particular reference to FIGS. 2 and 3, the air purifier 48 may include one or more perimeter exhaust vents 53, 55. The perimeter exhaust vents 53, 55 include areas within the air purifier 48 or areas within the carrier 51 that are configured to allow purified air to exit the air purifier 48 in an advantageous airflow pattern. Accordingly, they may be located around an edge or perimeter 57 of the sanitization station 28 or configured to direct air toward or in the direction of the edge or perimeter 57. The perimeter exhaust vents 53, 55 can include one continuous vent along or near the entire edge or perimeter 57, or a number of discrete vents around or near the edge. The airflow pattern created by the exhaust vents 53, 55 is advantageously an air curtain that at least partially surrounds the shielded seat 16, as represented by arrows 61, 63, 65, 67. With the perimeter exhaust vent 53 being located on the outer sanitizing side 52 and the perimeter exhaust vent 55 being located on the inner seat facing side 54, an air curtain can be created on both sides of the shield 10. In some embodiments, however, only one side may have an exhaust vent. Further, the concave contour 26 in the shield 10 can help form a more structured air curtain by encouraging air flow over the separation surface 20 via the Coandă effect.

The UVC sanitizer 50 can be included to further promote surface and/or air disinfection. The UVC sanitizer 50 can enable deep, automated disinfection of surfaces within the cabin 12 between and during rides, which is particularly beneficial in a ride sharing scenario. The UVC sanitizer 50 has a light source 64 that emits UVC light 66, and direct exposure to the UVC light can destroy a pathogen's DNA. In the illustrated embodiment, the UVC sanitizer achieves 3 log (99.9%) disinfection of *E-coli* in 5-10 minutes, depending at least partially on the target surface location and light source. The UVC light source 64 may be broad, such as a UVC light bulb to disinfect larger areas of the cabin 12. Or, the UVC light source 64 can be local, such as UVC LEDs which provide more localized surface disinfection within the cabin 12. In some embodiments, the sanitization station 28 includes both broad and local type light sources 64. The UVC sanitizer 50 can be integrated within the air purifier 48 so as to provide additional air sanitization in addition to surface sanitization. For example, UVC LEDs can be included in the air vent outlet 68 to sanitize and kill viruses in the air going through the air purifier 48. The UVC sanitizer 50 can be controlled by occupant detection, automation (e.g., time-based or vehicle status-based), and/or remote control. Further, it is possible to run the UVC sanitizer 50 in one area of the vehicle 14 while an occupant is present in another area (e.g., a driver runs the UVC sanitizer 50 after competing a drop-off). An HMI can be included to indicate disinfection status as it relates to UVC-based sanitization.

With particular reference to FIGS. 2 and 3, the sanitization station 28 serves as the structural hub or carrier 51 for the various components of the sanitizing shield 10. Accordingly, the panels 36, 38, 40, 42 can be joined to the sanitization station 28, whether removably as shown (e.g., via a screw, locking detent, or some other reversible attachment feature), or irremovably (e.g., welded or otherwise securely joined). Further, the various features of the sanitization station 28 can be either removably installed (e.g., clicked into a module or carrier 51) or more permanent (e.g., welded, bonded, or integrally formed into).

The sanitizing shield 10 can be anchored or otherwise attached at any operable location within the cabin 12, such as the back panel of the driver's seat 16, the driver's headrest 36, the ceiling of the vehicle 14, the floor of the vehicle, the center console armrest, the rear passenger seat 18, or a multipurpose box that replaces the front, non-driver passenger seat, to cite a few examples. Further, the separation surface 20 and/or the sanitization station 28 can be part of the seat structure such that they deploy directly from the seat 16, or they may be separate elements or components which are removable and fully detachable from the vehicle 14.

As illustrated, the inner seat facing side 54 of the sanitization station 28 can be used to facilitate installation of the sanitization station and separation surface 20 within the vehicle cabin 12. A clamp plate 70 is attached to the inner seat facing side 54 of the sanitization station 28 via two structural links 72, 74. The clamp plate 70 includes front and back plates 76, 78 which are configured to sandwich the headrest posts 80, 82. The structural links 72, 74 are pivotably attached to the back plate 78 of the clamp plate 70. Additionally, the structural links 72, 74 are pivotably attached to the inner seat facing side 54 of the sanitization station 28. This allows for relative movement between the separation surface 20 and the seat 16, which can help optimize flexibility in positioning of the sanitizing shield 10. A width or distance between the two structural links 72, 74 generally corresponds to a width or distance between the headrest posts 80, 82. This can help enhance structural stability of the overall shield 10 and seat 16 assembly. However, as addressed above, other configuration and mounting variations are certainly possible.

It is to be understood that the foregoing is a description of one or more embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "e.g.," "for example," "for instance," "such as," and "like," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation. In addition, the term "and/or" is to be construed as an inclusive OR. Therefore, for example, the phrase "A, B, and/or C" is to be interpreted as covering all the following: "A"; "B"; "C"; "A and B"; "A and C"; "B and C"; and "A, B, and C."

The invention claimed is:

1. A sanitizing shield for a vehicle, comprising:
   a separation surface configured to at least partially shroud a shielded seat, the separation surface having an inner seat facing side and an outer shielding side; and
   a centrally located sanitization station coupled to the separation surface, wherein the separation surface includes four or more removable panels directly attached to the centrally located sanitization station.

2. The sanitizing shield of claim 1, wherein the sanitization station includes a hand sanitizer dispenser.

3. The sanitizing shield of claim 2, wherein the hand sanitizer dispenser is located in a recessed wall of the sanitization station.

4. The sanitizing shield of claim 1, wherein the sanitization station includes an air purifier.

5. The sanitizing shield of claim 4, wherein the air purifier includes one or more perimeter exhaust vents.

6. The sanitizing shield of claim 5, wherein the separation surface is configured to create an air curtain that at least partially surrounds the vehicle seat.

7. The sanitizing shield of claim 6, wherein a concave contour in the separation surface is configured to create the air curtain.

8. The sanitizing shield of claim 1, wherein the sanitization station includes an ultraviolet-C (UVC) sanitizer.

9. The sanitizing shield of claim 1, wherein each removable panel of the four or more removable panels is made from a nonporous material.

10. The sanitizing shield of claim 1, wherein the sanitization station includes a carrier configured to accept a plurality of sanitization units.

11. The sanitizing shield of claim 10, wherein the plurality of sanitization units includes a hand sanitizer dispenser and an air purifier.

12. The sanitizing shield of claim 1, wherein the sanitization station has an inner seat facing side, and wherein a clamp plate is attached to the inner seat facing side of the sanitization station via a structural link that is configured to facilitate movement of the separation surface with respect to the vehicle seat.

13. The sanitizing shield of claim 1, comprising at least one perimeter exhaust vent configured to create an air curtain between the vehicle seat and the second vehicle seat.

14. A sanitizing shield for a vehicle, comprising:
a separation surface configured to at least partially shroud a shielded seat, the separation surface having an inner seat facing side and an outer shielding side; and
a sanitization station coupled to the separation surface, wherein the sanitization station includes an air purifier, wherein the separation surface is configured to create an air curtain that at least partially surrounds the shielded seat, and wherein at least one perimeter exhaust vent is located on an outer sanitizing side of the sanitization station and at least one perimeter exhaust vent is located on an inner seat facing side of the sanitization station.

15. The sanitizing shield of claim 14, wherein the separation surface includes a plurality of removable panels attached to the sanitization station.

16. The sanitizing shield of claim 15, wherein the plurality of removable panels is situated around a centrally located sanitization station.

\* \* \* \* \*